United States Patent [19]

Sherman

[11] Patent Number: 4,936,855
[45] Date of Patent: Jun. 26, 1990

[54] STEPPED-LOCK RING SYSTEM FOR IMPLANTABLE JOINT PROSTHESES

[75] Inventor: Randy G. Sherman, Austin, Tex.

[73] Assignee: Intermedics, Orthopedics, Inc., Austin, Tex.

[21] Appl. No.: 342,316

[22] Filed: Apr. 24, 1989

[51] Int. Cl.⁵ ............................ A61F 2/34; A61F 2/30
[52] U.S. Cl. ........................................ 623/22; 623/18
[58] Field of Search ................ 623/16, 18, 20, 19, 623/22, 23

[56] References Cited

U.S. PATENT DOCUMENTS

| | | | |
|---|---|---|---|
| 3,813,699 | 6/1974 | Giliberty | 623/22 |
| 4,365,358 | 12/1982 | Judet | 623/22 |
| 4,380,090 | 4/1983 | Romos | 623/22 |
| 4,624,674 | 11/1986 | Pappas et al. | 623/22 |
| 4,676,799 | 6/1987 | Legrand | 623/22 |
| 4,770,659 | 9/1988 | Kendall | 623/22 |
| 4,772,296 | 10/1979 | D'Errico | 623/22 |
| 4,798,610 | 1/1989 | Averill et al. | 623/22 |

Primary Examiner—David J. Isabella
Attorney, Agent, or Firm—John R. Merkling

[57] ABSTRACT

A prosthetic implant for use in replacing the ball end of a biological joint includes a cup member for insertion into the natural socket, an insert received in the cup member defining a ball receiving cavity with a stepped entry, and a split locking ring received in the stepped entry. A ball shaped portion of a prosthesis introduced into the entry will displace the locking ring inwardly to a larger stepped portion of the entry where the locking ring can expand to allow passage of the ball after which the ring contracts and slides over the ball to a locking position in a smaller stepped entry portion.

17 Claims, 2 Drawing Sheets

1

STEPPED-LOCK RING SYSTEM FOR IMPLANTABLE JOINT PROSTHESES

BACKGROUND OF THE INVENTION

1. The Field of the Invention

The present invention relates to implantable prosthetic joint devices for application in the human body. More particularly the present invention is directed to a prosthetic device which can be readily assembled and disassembled in place so as to assure proper fit.

2. Description of the Prior Art

The pelvis in the human body contains two hip bones, one on each side of the body, each containing an acetabulum or hip socket for receiving and forming a seat for the femoral head or ball of the femoral or thigh bone. The femoral head is connected to the thigh bone by a neck which is angularly disposed relative to the axis of the femoral and relative to the vertical axis of the body. Thus any load applied by the body through the hip and femoral neck to the thigh bone and leg and any impact, such as caused by walking, jumping and the like applied by the leg and thigh bone through the femoral neck and hip to the body, is transmitted angularly through the femoral neck. This angular transmission of the load and forces through the femoral neck results in high stresses and high sheer-loads applied to the femoral neck. These high stresses, when normally applied can cause dislocation of the femoral head from the acetabulum or hip socket and fracture and breaking of the femoral neck. In older people such femoral neck often becomes brittle and in both older and younger people is subject to injury. Replacement is often required.

The utilization of prosthetic devices which are implanted into the human body for replacing defective, damaged or diseased joints of the type described above have been well known. One known specific form of prosthetic device is for use in replacing anatomical joints of the body having ball and socket characteristics, as for example the above-discussed hip joint. Such a prosthesis essentially provides a detachable inner-connection between the femoral and the acetabulum socket of the pelvis which serves the purpose of accomplishing the universal-type movement associated with the replaced natural biological joint. Conventional prosthetic hip joints normally embody an acetabulum-type cup member having a spherical cavity, which may be suitably secured in a variety of ways to the acetabulum pocket of the pelvis, and an artificial femoral head which is appropriately attached to the femoral. The femoral insert includes a smooth and substantially spherical head member which mates with and is rotatably supported by the spherical cavity of the cup member. As a result of this structural inner-relationship, a ball and socket-type joint is created which permits ordinary-type of articulated motion associated with the human hip joint.

In this particular field there are several known approaches for forming such artificial joints. Specific reference is made to U.S. Pat. Nos. 3,813,699; 4,044,403; 4,380,090; and 4,624,674. Each of these patents show and describes femoral heads and necks for surgical implants as replacements for damaged or broken natural heads or necks. In each such device an outer spherical metal cup having an inner plastic insert, is provided for implanting into the acetabulum or hip socket. The inner plastic insert has a socket into which the metal sphere, having a neck and a stem for connection to the thigh bone, is pivotally received.

While these devices have generally served their desired function, they have not been entirely without problems. One of the primary problems is in achieving the proper size combination of the prosthetic components so that the femoral head will regain its proper orientation with respect to the hip as a whole. In order to provide for size adjustment, the prosthetic device must be capable of being assembled in the operating room with a degree of facility and ease that has not been found in the previous devices, many of which are pre-assembled using fairly difficult assembly techniques. It is the intention of the '403 patent mentioned above, to provide a prosthesis which will result in a firm non-dislocatable joint. In contradistinction, the '463 patent has as its object to provide a prosthetic joint which, when dislocated by an unusual action, can be properly relocated by non-invasive techniques.

SUMMARY OF THE INVENTION

It is the intention of the present invention to form an implantable joint prosthesis having a bi-polar component which can be easily field assembled and disassembled. The present invention provides positive and secure inter-connection between the femoral head and the acetabulum component, provides adequate range of pivotal movement, provides low effort assembly and disassembly of the components and provides immediate intra-operative interchangeability of components.

BRIEF DESCRIPTION OF THE DRAWINGS

The present invention will now be described by way of example with reference to the accompanying drawings in which.

DETAILED DESCRIPTION OF THE INVENTION

Figure 1:
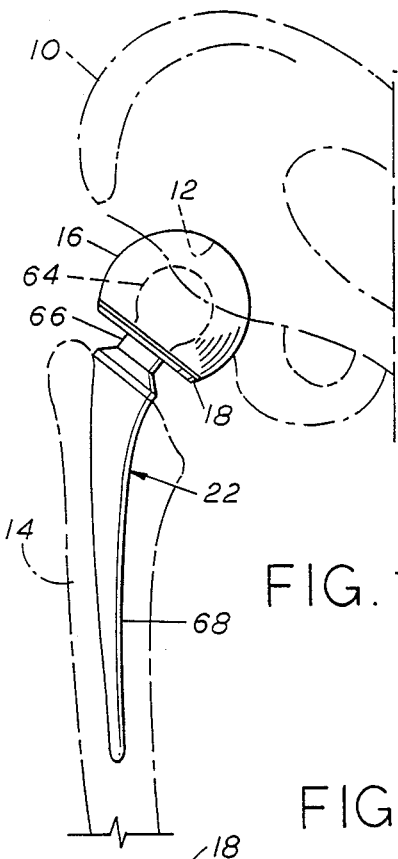
FIG. 1 is a front elevation showing, in phantom lines, the natural pelvis, acetabulum, and thigh bone and, in full lines, the implant device of the instant invention.

Referring now to the FIGURES and particularly to FIG. 1, the pelvis, generally designated at 10, has an acetabulum or hip socket 12 which normally receives the head or ball (not shown) of the femoral 14. The subject prosthesis includes a cup 16, an insert 18, a locking ring 20 and a femoral implant 22.

The cup 16, insert 18, locking ring 20 and femoral implant 22 may be formed from any of the known materials compatible with bone and body tissue of the patient and must be of sufficient strength to withstand the normal forces which are encountered. Preferably the cup 16 is of one piece construction of metal, such as Ti-6AL-4V alloy or impact, wear and abrasive resistant ceramic material. The insert 18 and locking ring 20 are preferably made from the same low-friction plastics material having sufficient strength, abrasive resistance and rigidity to accommodate forces which would be likely to be applied to the front. The femoral implant 22 preferably is of metal such as the above mentioned alloy. Cobalt chrome molybdenum alloy ASTM F-75 and stainless steel ASTM F-139-71 are also suitable for this purpose.

Figure 2:
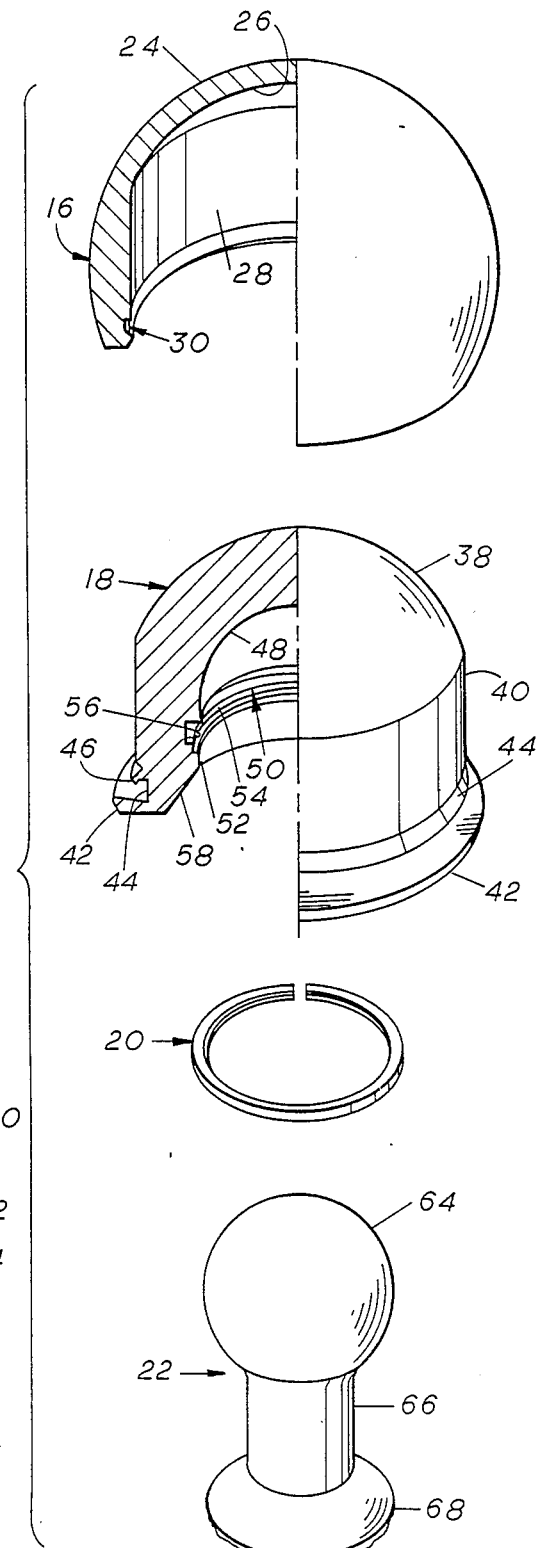
FIG. 2 is an enlarged exploded perspective view of the components of the present invention.
Figure 3:
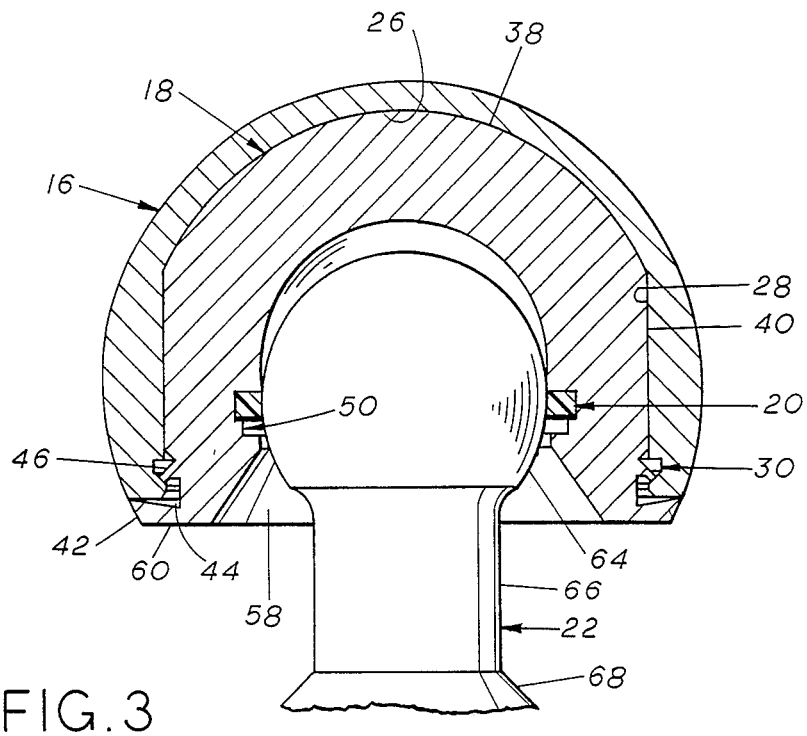
FIG. 3 and 4 are like sections through the outer spherical cup, the plastic insert and locking ring showing the metal sphere of a femoral implant partially and fully inserted, respectively, therein.
Figure 4:
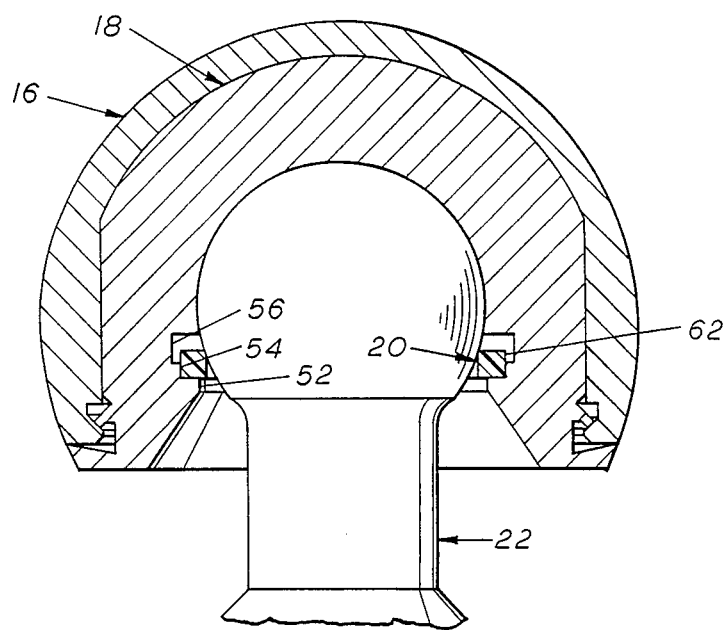

Referring now to FIGS. 2, 3 and 4 the spherical cup 16 has an outer spherical surface 24 and an inner spherical dome 26 at the inner end of a cylindrical channel 28. Adjacent the open end of the cylindrical channel 28 is an inwardly directed annular groove 30 having a generally trapezoidal section formed by first wall 32 extending normal to channel 28, second wall 34 parallel to channel 28, and third wall 36 defining a truncated conical surface. The outer surface of the insert 18 is shaped to the inner configuration of the inner surface of the spherical cup 16. Thus, the insert 18 has an outer spherical dome 38 and a downwardly extending outer cylindrical skirt 40 with a radially outwardly extending integral flange 42 at the free end thereof. Immediately adjacent the flange 42 there is an outwardly directed annular recess 44 in which is located an integral lock 46 which comprises a downwardly and outwardly extending flexible ridge. The lock 46 is aligned to engage the third wall 36 of the annular groove 30 of the cup 16 thereby resisting withdrawal of the insert 18 from the cup 16.

The inner surface of the insert 18 is domed at 48. Below the dome 48 and forming an entry way thereto, is a cylindrical portion 50 formed by stepped annular surfaces 52, 54, 56, with surface 52 being of the smallest diameter and furtherest from the dome 48 and surface 56 being the largest diameter and most closely adjacent the dome 48. A conical lead-in surface 58 extends between the annular surface 52 and the bottom surface 60 of the insert.

Figure 5:
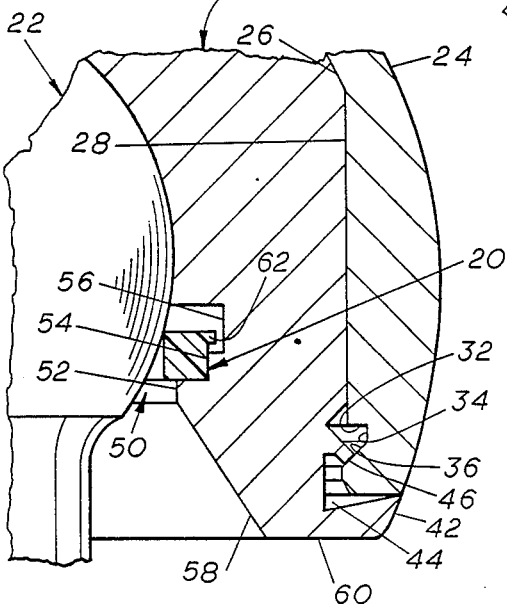
FIG. 5 is an enlarged detail of the stepped recess and locking ring shown in section of FIGS. 3 and 4.

The locking ring 20, as best seen in FIG. 5, has a generally square section with an integral outwardly directed flange 62 on the upper edge thereof. All of the remaining edges have a slight chamfer to prevent feathering from occurring. The locking ring 20 is mounted in the cylindrical entry portion 50 by compressing it sufficiently to pass through annular surface 52 with the natural expansion of the ring 20 holding it in the intermediate stepped-surface 54 with flange 62 lying in the annulus formed by stepped wall 56. The purpose of this flange is to prevent the locking ring 20 from being tilted to either release the ball of the implant or to be drawn out through the entry way 50.

The femoral implant 22 is a metal member having a head or ball 64, a neck 66 and a stem 68. The implant 22 can be either a unitary member or be provided with, a modular head or ball in the known manner.

The operation of the present invention can be best appreciated from FIGS. 3 and 4. In FIG. 3 the ball 64 is shown being passed through cylindrical portion 50 towards dome 48. The split locking ring 20 is forced from the intermediate stepped-surface 54, where it normally is seated, to the largest stepped-surface 56 where it is provided with room for sufficient expansion to allow the ball 64 to pass therethrough. When the ball 64 is completely seated in the dome 48, as shown in FIG. 4, then the locking ring 20 will contract, by its natural resiliency, and slide along the surface of the ball 64 to resume its initial position on the intermediate surface 54. In this position it will prevent the unintended withdrawal of the ball from the dome. Because of the annular flange 62, the locking ring 20 will be prevented from twisting and possibly becoming dislodged from the entry portion 50.

It will also be appreciated that this type arrangement allows for a ready removal of the ball for exchange, should there be a need to substitute a different and/or better fitting femoral implant 22 having a longer or shorter neck; a greater or smaller angle; with a longer or shorter; thicker or thinner stem, until the prosthesis is correct for the patient. All that is needed for removal of the ball is insertion of a tool (not shown) against the locking ring 20 pushing it inward from surface 54 until it seats in the larger surface 56 where it can expand to and allow withdrawal of the ball 64 through entry 50. This maneuver can be easily accomplished by the orthopedic surgeon without the requirement expensive tooling, alignment of slots or engagement with slots, as is frequently the case when dealing with prosthetic devices of the prior art.

FIG. 5 shows in detail, the locking configuration which is achieved between the cup 16 and insert 18. The lock 46 makes contact with surface 46 forming a snap lock between the cup and insert. The details of the above-discussed locking -ring 20 and stepped entry 50 are also shown.

The present invention may be subject to many modifications and changes without departing from the spirit or essential characteristics thereof. The foregoing description should therefore be considered in all respects as illustrative and not restrictive as to the scope of the present invention.

I claim:

1. An implantable prosthetic joint for use in replacement of a ball end of a biological joint, said prosthetic joint comprising:
   a cup member for insertion into and seating in a natural socket of the joint;
   a bearing member receivable in said cup member and having an inner ball receiving surface wherein said ball receiving surface defines a spherical dome at an inner end of a profiled generally cylindrical entry, said generally cylindrical entry comprising a plurality of annular steps with the largest diameter step proximal to the dome end and the smallest diameter stop being distal from the dome end and forming an opening to said entry;
   a locking ring member received in at least some of said annular steps; and
   a bone implant member having a ball on a free end thereof, said ball being receivable in said dome through said entry, said locking ring lying in said annular steps and engaging said ball to hold said prosthesis in an assembled condition.

2. An implantable prosthetic joint according to claim 1, wherein there are three steps, said locking ring normally lying in an intermediate step of said steps.

3. An implantable prosthetic joint according to claim 1, further comprising: a truncated conical entry way leading to said profiled cylindrical entry.

4. An implantable prosthetic joint according to claim 1, wherein said bearing member is formed from a biocompatible material.

5. An implantable prosthetic joint according to claim 4, wherein said material is plastic.

6. An implantable prosthetic joint according to claim 1, wherein said bearing member and said locking ring are formed of the same biocompatible material.

7. An implantable prosthetic joint according to claim 1, wherein said locking ring is a split ring having a generally rectangular section with an integral, outwardly directed, radial flange on one edge thereof.

8. An implantable prosthetic joint according to claim 1, wherein said profiled generally cylindrical entry comprises:
- first, second and third annular steps increasing in diameter toward said dome, said first step forming an opening to said entry and said locking ring normally lying in said second step;
- said locking ring having a generally rectangular section with an integral outwardly directed radial flange on one edge thereof;
- said locking ring being so dimensioned that said flange extends beyond said second step thereby preventing said locking ring from twisting in such manner as to become dislodged from said entry.

9. An implantable prosthetic joint according to claim 1, wherein said bone implant member has a stem with a neck extending at an angle from one end thereof, said ball being mounted on said neck.

10. An implantable prosthetic joint according to claim 9, wherein said bone implant member is of unitary construction.

11. An implantable prosthetic joint according to claim 1, wherein said bone implant member and said cup member are both formed from biocompatible metal.

12. An implantable prosthetic joint for use in replacement of a biological joint, said prosthetic joint comprising:
- a first assembly received in a natural socket of the joint and having at least a bearing member having an inner surface defining a generally spherical cavity with an entry formed by first, second, and third progressively larger annular steps leading to said cavity, and a locking ring mounted in said entry normally lying in said second step; and
- a second assembly forming a bone implant member and having a ball portion on one end thereof receivable in said cavity, whereby as said ball is introduced into said entry said locking ring is driven to said third step where it expands to allow passage of said ball therethrough and contracts after passage of the major diameter of said ball to return to the second step locking said assemblies together.

13. An implantable prosthetic joint according to claim 12, wherein said locking ring is a split ring dimensioned to normally lie in said second step, said ring having an integral radial flange on one end extending into said third step at all times whereby said ring is prevented from twisting so as to become dislodged during entry of said ball into and removal of said ball from said cavity.

14. An implantable prosthetic joint according to claim 12, wherein said first annular step has a diameter at least as large as said ball.

15. An implantable prosthetic joint according to claim 12, wherein said second annular step is at least as large as the outer diameter of said locking ring in normal conditions, said locking ring having an inner diameter smaller than said first annular step and a thickness greater than said second annular step.

16. An implantable prosthetic joint according to claim 12, wherein said third annular step has a diameter at least large enough to allow said locking ring to expand sufficiently for its inner diameter to allow passage of said ball therethrough.

17. A method for assembling and disassembling members of an implantable prosthetic joint, one of said members being received in a natural socket of the joint and having an inner surface defining a cavity with a progressively enlarging annular three-stepped entry leading to a ball receiving generally spherical dome, a bone implantable second member having a ball portion receivable in said dome, and a locking ring third member having an outer diameter approximately that of the second step and an inner diameter less than said ball, comprising the steps of:
- positioning said locking ring member in the second step of said entry restrained by the first step;
- introducing said ball into said entry driving said locking ring to the largest third step where it expands sufficiently to allow the major diameter of said ball to pass therethrough and thereafter said locking ring contracting and returning to seat in said second step.

* * * * *